United States Patent [19]
Adelberg et al.

[11] Patent Number: 6,077,299
[45] Date of Patent: Jun. 20, 2000

[54] NON-INVASIVELY ADJUSTABLE VALVE IMPLANT FOR THE DRAINAGE OF AQUEOUS HUMOR IN GLAUCOMA

[75] Inventors: Daniel A. Adelberg, Scottsdale, Ariz.; Paul S. Schluter, Whitefish Bay, Wis.

[73] Assignee: Eyetronic, LLC, Scottsdale, Ariz.

[21] Appl. No.: 09/102,022

[22] Filed: Jun. 22, 1998

[51] Int. Cl.[7] .............................. A61F 2/48; A61M 5/00
[52] U.S. Cl. ................................................ 623/24; 604/9
[58] Field of Search .................................. 623/24, 12, 2, 623/4, 5; 604/9, 294, 296, 297, 8

[56] References Cited

U.S. PATENT DOCUMENTS

| | | | |
|---|---|---|---|
| 3,926,175 | 12/1975 | Allen et al. ................................. | 128/1 |
| 4,457,757 | 7/1984 | Molteno . | |
| 4,604,087 | 8/1986 | Joseph . | |
| 4,987,897 | 1/1991 | Funke . | |
| 5,071,408 | 12/1991 | Ahmed . | |
| 5,129,394 | 7/1992 | Mehra . | |
| 5,213,098 | 5/1993 | Bennett et al. . | |
| 5,273,518 | 12/1993 | Lee et al. . | |
| 5,366,506 | 11/1994 | Davis ........................................ | 623/12 |
| 5,411,473 | 5/1995 | Ahmed . | |
| 5,423,334 | 6/1995 | Jordan ..................................... | 128/899 |
| 5,454,796 | 10/1995 | Krupin . | |
| 5,487,760 | 1/1996 | Villafana .................................... | 623/2 |
| 5,554,177 | 9/1996 | Kieval et al. . | |
| 5,564,434 | 10/1996 | Halperin et al. . | |
| 5,626,558 | 5/1997 | Suson . | |
| 5,743,869 | 4/1998 | Ahmed ........................................ | 604/9 |
| 5,814,100 | 9/1998 | Carpentier et al. ......................... | 623/2 |

FOREIGN PATENT DOCUMENTS 128703  12/1984  European Pat. Off. .

OTHER PUBLICATIONS

Four–page brochure entitled: "*The Ahmed Glaucoma Valve*", New World Medical.

"*Textbook of Glaucoma*", by M. Bruce Shields, M.D., Fourth Edition, pp. 158–163.

"*Drainage Implant Surgery*", by M. Bruce Shields, M.D., Williams & Wilkings, 1998, pp. 538–546.

Four–page brochure entitled: "*Eye Valves For Surgical Management of Complex Glaucomas*", Hood Laboratories Aug. 1995.

Six–page brochure entitled: "*OptiMed Glaucoma Pressure Regulator–Model 1014*", Tecfen.

"*Glaucoma A Colour Manual of Diagnosis and Treatment*", by J. Kanski, et al., Buterworth–Heinemann, Second Edition, pp. 158–163.

*Primary Examiner*—Mickey Yu
*Assistant Examiner*—Alvin Stewart
*Attorney, Agent, or Firm*—Fitch, Even, Tabin & Flannery

[57] ABSTRACT

A medical implant valve, for example, a glaucoma valve, is configured to be non-invasively adjustable. A rotor is operatively coupled to the valve to enable the position of valve to be adjusted between an open and closed position; the rotor being responsive to a magnetic field. An external instrument is used to control rotation of the rotor.

15 Claims, 7 Drawing Sheets

NON-INVASIVELY ADJUSTABLE VALVE IMPLANT FOR THE DRAINAGE OF AQUEOUS HUMOR IN GLAUCOMA

BACKGROUND OF THE INVENTION

The present invention relates to implantable medical valves, and in particular, to ophthalmic devices for the relief of the high intraocular pressures characteristic of glaucoma.

DESCRIPTION OF THE RELATED ART

Glaucoma is a disease characterized by elevated intraocular pressure which may lead to nerve damage and loss of vision if left untreated. Pressures in the range of 16±3 mm Hg up to about 21 mm Hg are considered normal, whereas pressures substantially above that range are considered abnormally high. Over a period of time, the high pressures may cause the optic nerve to become damaged, leading to a narrowing of the field of vision and eventually to blindness if not appropriately treated.

Medical therapy to reduce the intraocular pressure by improving the outflow or reducing production of aqueous humor is important in the management of glaucoma. Such treatments may consist of topical ophthalmic or systemic oral medications. Such treatments may be limited in their effectiveness, however, due to high cost, poor patient compliance and, potentially, patient allergies. In addition, side effects, such as exacerbation of underlying cardiac and pulmonary disorders, renal stones and blood dyscrasias have been documented.

Current surgical management of glaucoma includes laser trabeculoplasty, filtration surgery via trabeculectomy, ciliary body ablation and glaucoma aqueous shunt implants. Over the past decade, adjunctive chemotherapeutic agents, such as fluorouracil and mitomycin, have been incorporated with trabeculectomy to improve the short and long term effectiveness of intraocular pressure reduction. The use of such agents, however, increases the likelihood of potentially sight threatening postoperative complications, such as hypotony maculopathy, suprachoroidal hemorrhage and endophthalmitis.

One method of treating glaucoma is to implant an artificial drainage shunt that allows the aqueous humor to flow from the anterior chamber of the eye to the sub-Tenon's space where it is absorbed. Almost all shunts include a tube attached to a posterior episcleral explant. Some shunts further contain a pressure-sensitive valve for restricting aqueous flow.

Many of the devices in use today are based on the design described by Molteno in U.S. Pat. No. 4,457,757. The Molteno device incorporates a scleral plate to promote formation of a functioning bleb in the sub-Tenon's space. The plate has an inlet tube that extends into the anterior chamber of the eye, allowing the aqueous humor to flow from the anterior chamber to the plate where it is absorbed. The Molteno plate does not have a mechanical pressure regulating mechanism, but instead relies on the pressure regulation provided by the resistance to aqueous flow and total surface area of the tissue capsule that forms above the scleral plate. A problem with the earlier Molteno device, however, is that the aqueous humor is rapidly absorbed during the first few days after surgery and can cause the intraocular pressure to fall to unacceptably low levels that can damage sight.

Other artificial drainage shunts, such as described in White, U.S. Pat. No. 4,554,918, Joseph, U.S. Pat. No. 4,604,087 and Krupin, U.S. Pat. No. 5,454,796, incorporate a unidirectional valve to prevent backflow of aqueous humor and provide to a limited extent resistance to aqueous flow. In a glaucoma shunt disclosed by Ahmed in U.S. Pat. No. 5,411,473, a mechanical pressure regulating valve is added to the basic Molteno design. The valve is designed to open for pressure differences greater than 10 mm Hg and provide some protection against excessive aqueous outflow during the first few days after surgery, as well as providing long-term pressure regulation.

Several shunts have used removable ligatures or plugs to prevent flow of aqueous humor during the initial period after implantation, but this method requires a follow-up procedure to remove the ligature or plug. Other shunts have employed biodegradable sutures or plugs but these have been less than satisfactory because they do not always dissolve. In a glaucoma shunt disclosed by Suson in U.S. Pat. No. 5,626,558, one end of a thin tube initially sealed is inserted into the anterior chamber of the eye and the other end, always open, serves an outlet for the aqueous humor. After a fibrous capsule has formed during the initial postimplantation period, perforations are made at the sealed end of the tube to enable flow of aqueous humor through the device. The flow rate can be increased by placing additional perforations along the tube, preferably with a laser. Although this method provides the ability to increase the flow of aqueous humor by adding more perforations, the adjustment procedure is complex and moderately invasive.

Accordingly, it is desirable to have a pressure regulating valve that can be non-invasively adjusted to regulate at a higher pressure during the first few days after surgery and then reduced over a period of weeks to its long-term value.

SUMMARY OF THE INVENTION

These problems and the prior art are overcome in large part by an externally adjustable valve implant according to the present invention which can be used to treat glaucoma by regulating the flow of aqueous humor from the anterior chamber of the eye to relieve excess pressure. The implant is sutured to the eye and covered by a smooth layer of the patient's tissue, known as the Tenon's capsule, as well as donor tissue, such as sclera, which covers the extraocular portion of the tube. The implant has a small inlet tube that is surgically inserted in the anterior chamber of the eye allowing aqueous humor to flow from the anterior chamber to the valve. An alternative surgical approach is the insertion of the tube into the posterior chamber vitreous cavity through the pars plana. After passing through the pressure and/or flow regulating value in the implant, the fluid is dispersed along the periphery of the implant to the interior of the Tenon's capsule where it is absorbed by the body. In one embodiment, the valve inhibits flow below and allows flow above a specific pressure difference between the intraocular pressure within the eye and the pressure within the bleb cavity in Tenon's capsule. The specified pressure difference or set-point is always positive and the valve is always closed for negative pressure differences to prevent reverse flow of fluid from the Tenon's capsule back into the anterior chamber of the eye.

An important aspect of this invention is that the pressure flow characteristic can be adjusted in a non-invasive manner. In one embodiment, the set-point is adjusted by rotating an external magnet positioned near the implant. The rotating magnetic field causes a freely rotating magnetic or magnetizable rotor in the implant to rotate synchronously with the applied external field. A series of speed reducing torque-enhancing gears drive an armature plate that precisely deflects one wall of the cavity containing the pressure and/or flow regulating valve. The pressure and/or flow regulating valve is designed to be responsive to the cavity wall deflection. In one embodiment, using a pressure regulating valve, the pressure set-point can be increased or decreased depending on the direction of rotation of the magnet and the adjustment can be repeated any number of times.

The ability to non-invasively adjust the valve provides several benefits in regulating the flow of aqueous humor in glaucoma patients with implantable shunts. Immediately after the device is implanted, there is a period of several days during which the aqueous humor is readily absorbed into the Tenon's tissue overlying the implant. The excess absorption can cause the pressure within the eye to fall to an unacceptably low level which may result in complications that can damage sight. An implant with an adjustable pressure set-point can be set to a higher pressure set-point for the first few days after surgery to minimize the risk of these complications. An adjustable valve also allows a lower aqueous flow to be selected during the initial period after surgery to promote the growth of a fibrous capsule with optimal filtering properties. After the initial period, the pressure set-point can be gradually reduced to the desired long-term value. In conjunction with external IOP measurements, the adjustable valve makes it possible to compensate for an individual patient's response to surgery and medications including subsequent changes in the pressure flow characteristics of the bleb cavity and surrounding Tenon's tissue as well as changes in aqueous fluid production. To compensate for changes in the properties of the implant due to partial occlusion of the inlet tube, valve and distribution channel by particulate and infiltration by body tissue; and to compensate for variability in the manufacture of the valve.

A further aspect of this invention is that setting of the valve can be interrogated by an external device. The implant contains a resonant circuit whose resonant frequency varies according to the setting of the valve. In one embodiment, this is accomplished by using a fixed inductor including one or more loops of wire connected to a variable capacitor whose capacitance is governed by the angular rotation of the same armature plate that modifies the setting of the valve. The inductive loop also serves as an antenna and allows the resonant frequency of the implant to be probed with a dip meter or other resonant absorption sensing circuit or device. The rotating magnet and resonant sensing circuit may be combined in a single hand-held instrument.

The ability to interrogate the absolute valve setting provides several benefits. It verifies that the rotating magnetic field has successfully coupled to the rotor in the implant and that the valve has been adjusted. Second, it provides a self-contained and non-volatile record of the valve setting and does not strictly depend upon other medical records for safe and effective use. Third, it is possible to determine that the valve is operating at or near its minimum or maximum setting providing useful information for subsequent therapy. Fourth, the ability to interrogate the valve setting is a useful diagnostic tool for manufacturing and testing the device and for testing the device prior to implanting it.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 7:
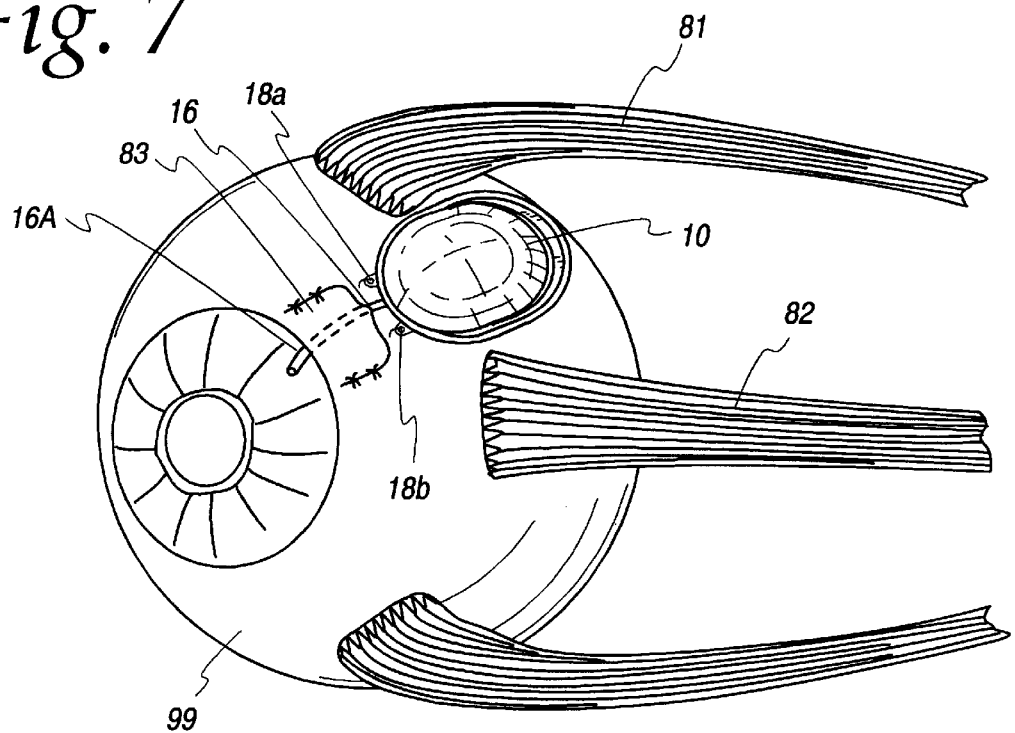
FIG. 7 is a perspective view of the implant fitted to the eye of a patient.
Figure 8:
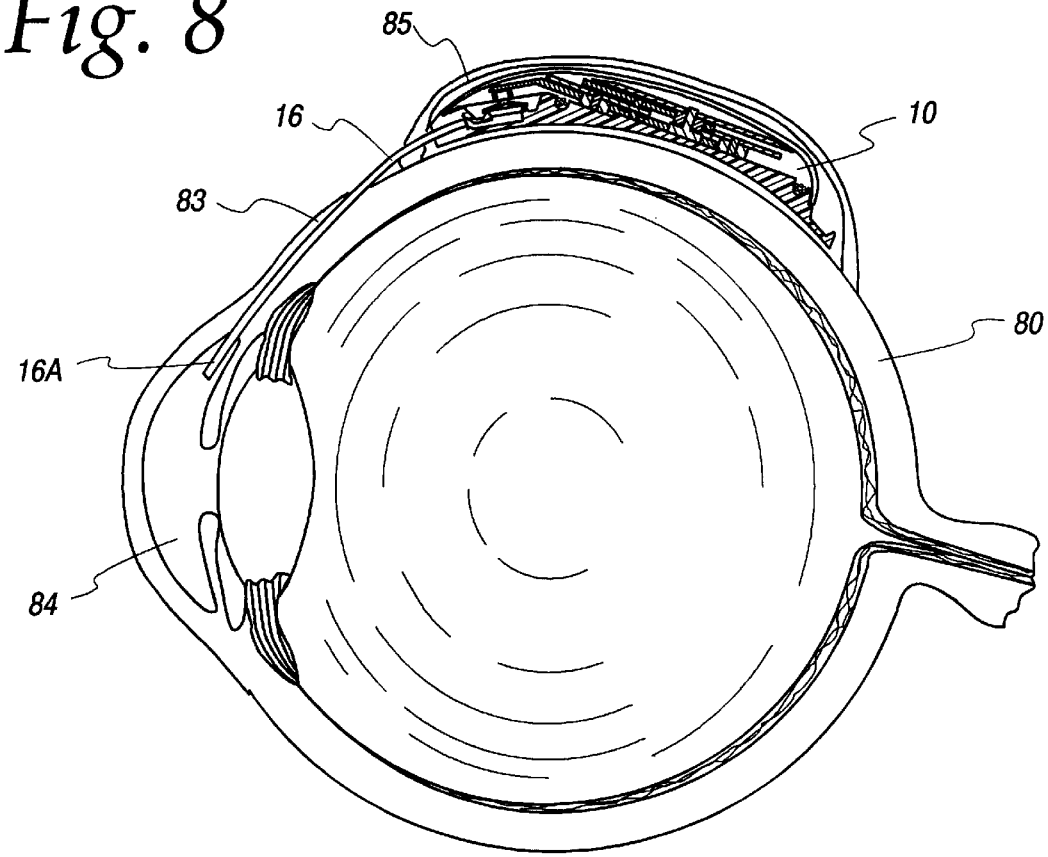
FIG. 8 is a cross-sectional view of the implant and the eye of a patient.

Turning now to the drawings and with particular attention to FIGS. 7 and 8, an adjustable medical valve 10 according to an embodiment of the present invention is shown in position on a patient's eye 99. In particular, the adjustable medical valve 10 includes an inlet tube 16 with an end 16a. The adjustable medical valve 10 includes a pair of eyelets 18a, 18b used to enable suturing of the valve to the patient's eye. In particular, the eyelets 18a and 18b are used for suturing the valve to the sclera 80 to anchor it between the extra-ocular superior rectus 81 and the lateral rectus 82 muscles of the eye 99. The free end 16a of the inlet tube is surgically inserted under a scleral flap 83 and into the anterior chamber 84 of the eye. As will be discussed in greater detail below, aqueous humor in the anterior chamber 84 of the eye enters the free end 16a of the inlet tube 16 where it passes into a chamber in the adjustable medical valve 10 to eventually be absorbed by the sub-Tenon's tissue 85 which forms above the implant 10.

Figure 1:
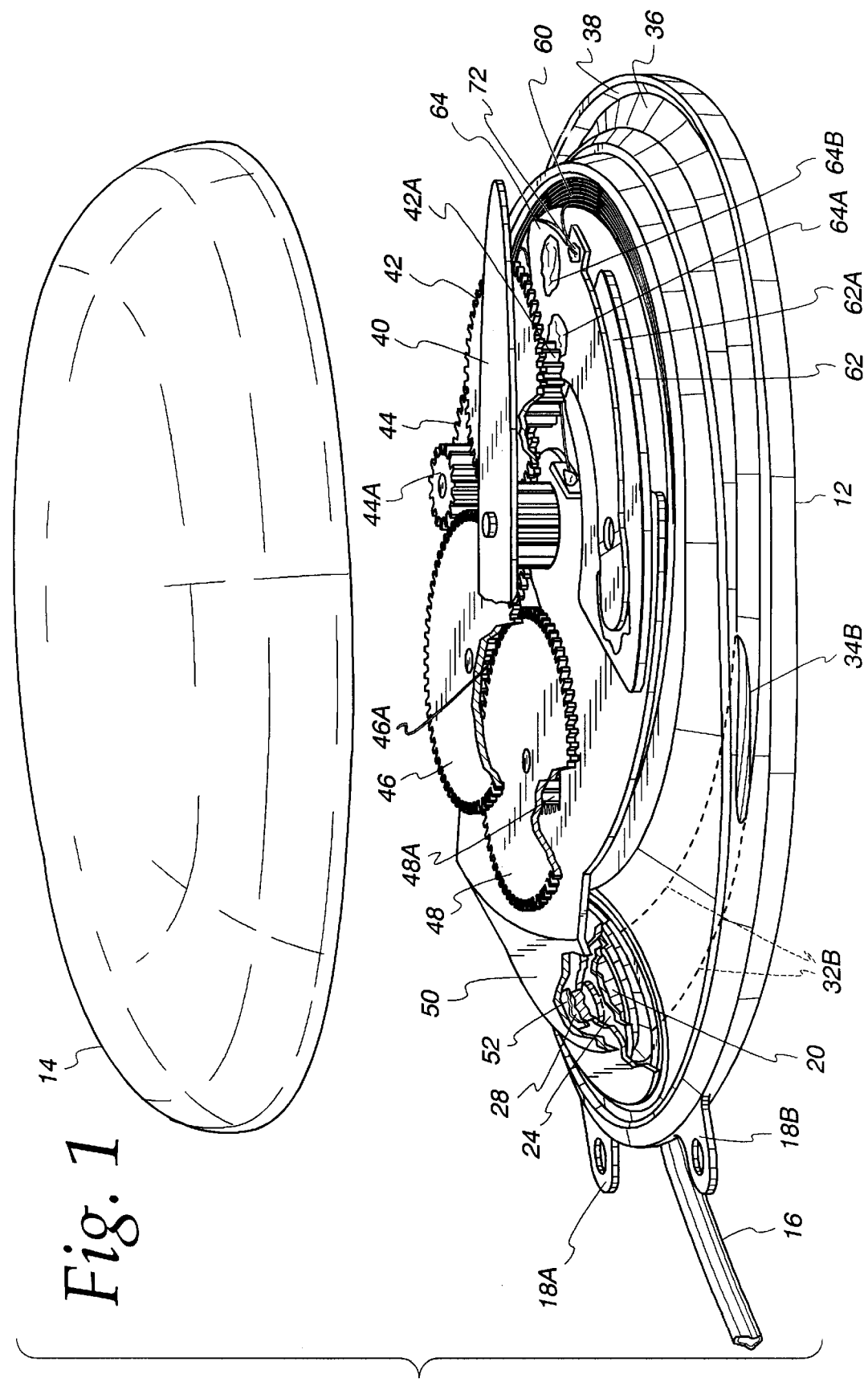
FIG. 1 is a perspective view of an adjustable valve implant according to an embodiment of the present invention.
Figure 2:
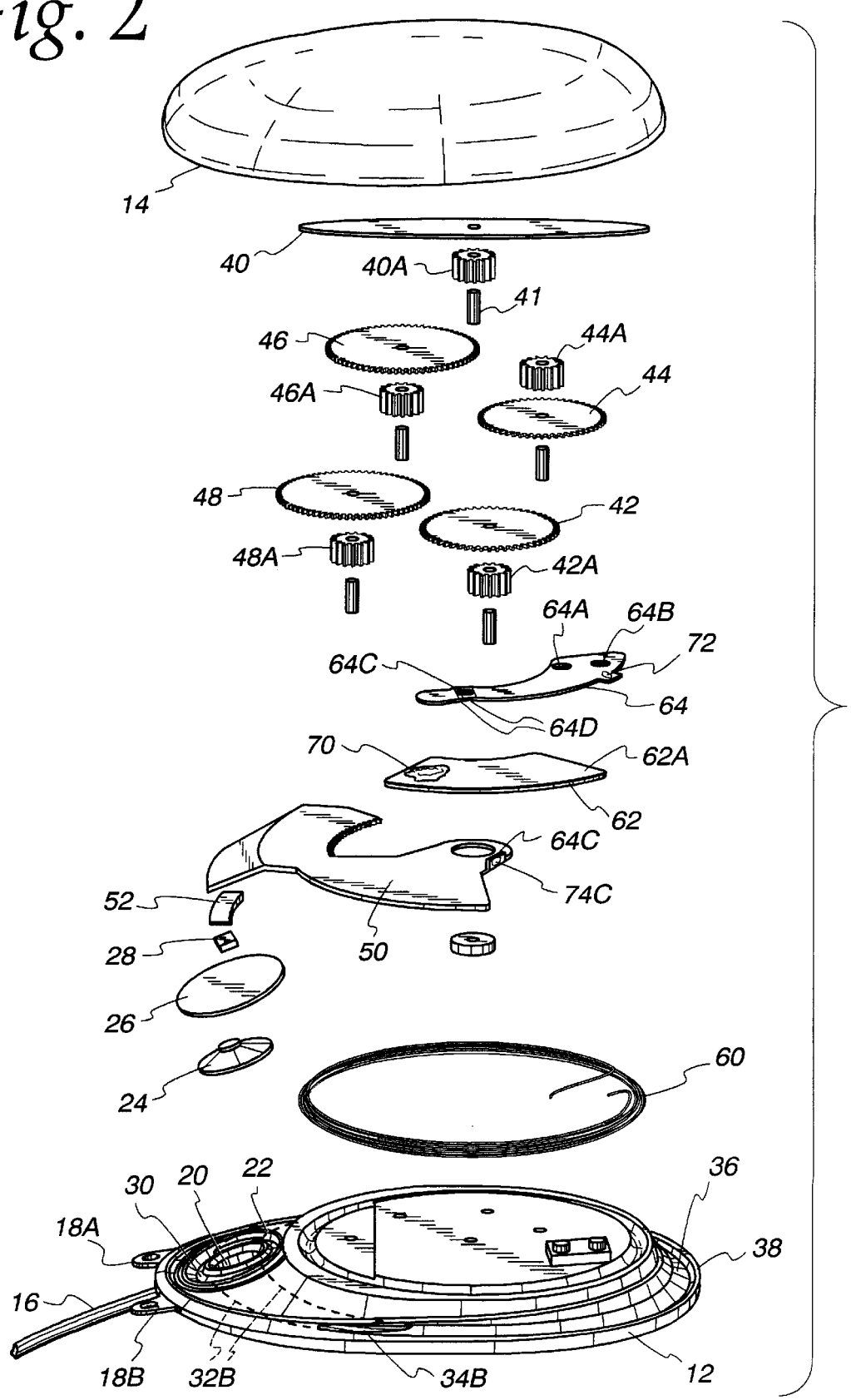
FIG. 2 is an exploded perspective of the adjustable valve implant of FIG. 1.
Figure 3:
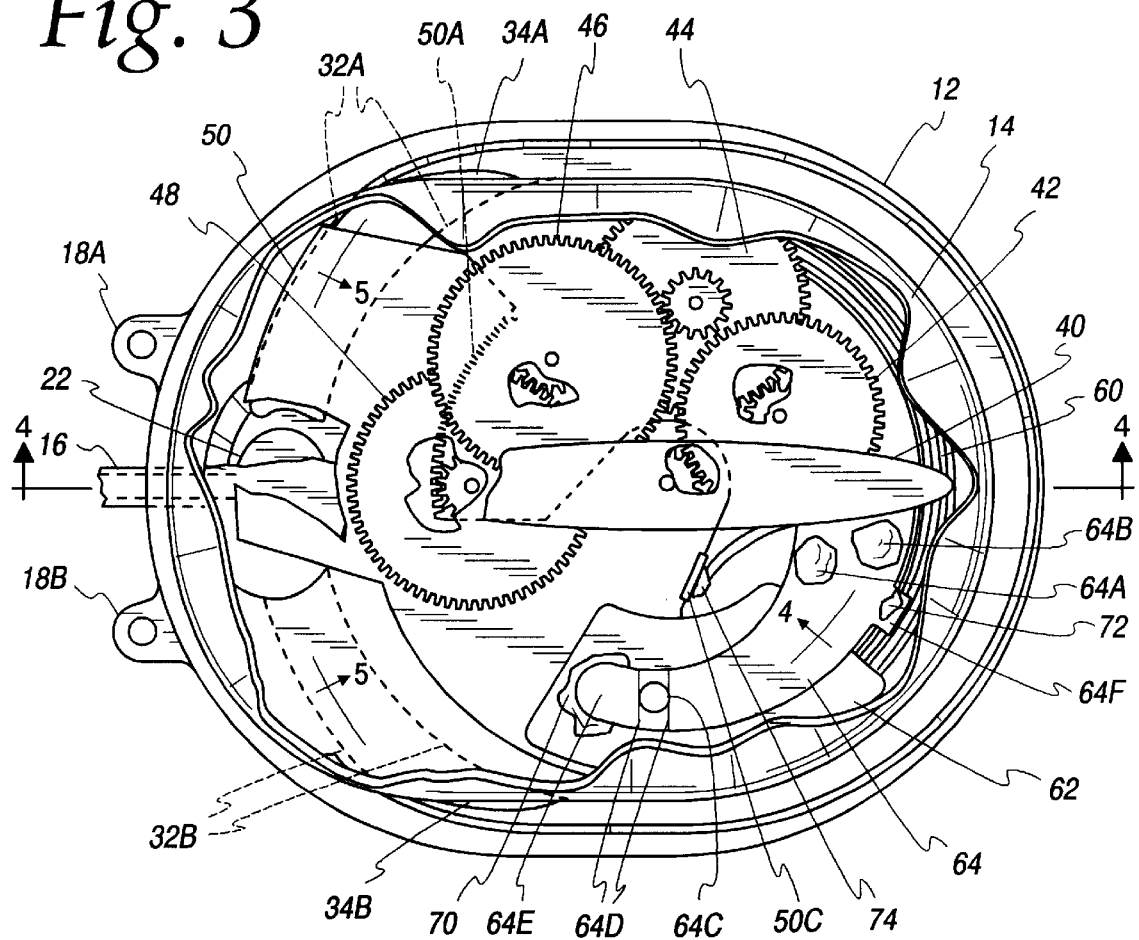
FIG. 3 is a plan view of the adjustable valve implant.
Figure 4:
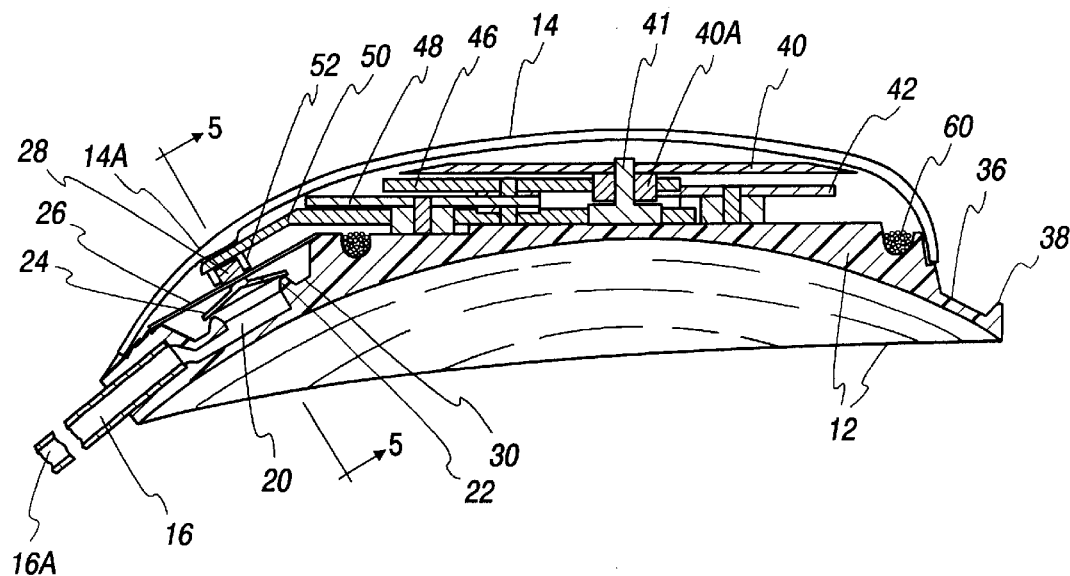
FIG. 4 is a cross-sectional view of the adjustable valve implant.

The adjustable medical valve 10 according to the present invention is illustrated in greater detail with reference to FIGS. 1–4. In particular, the adjustable medical valve 10 includes a base plate 12, a cover 14 and an inlet tube 16. As shown, the base plate 12 has a generally oval shape and an inner surface (FIG. 4) that is formed to generally conform to the nominal radius of the eye 99. The base plate 12 further includes a peripheral rim 38 which defines a drainage channel 36 around the perimeter of the posterior half of the base plate 12. A pair of eyelets 18a and 18b are formed on the anterior side of the base plate, and as discussed above, are used for suturing the adjustable medical valve 10 to the sclera 80. The adjustable medical valve 10 further includes a small chamber 20 whose effective cross-sectional area is defined by an internal raised rim 22. A pressure-sensitive valve 24 is provided, typically made of the flexible material such as silicone, in the shape of a flat cone, such that the outer perimeter of the cone presses against the rim 22 (FIGS. 3 and 4). The small chamber 20 is surrounded by a surrounding chamber 30 (FIG. 2) which is operably accessible to the small chamber 20 via opening and closing of the valve 24. The surrounding chamber 30 is sealed from the interior of the implant by a flexible diaphragm 26 hermetically bonded to the base plate 12.

A pair of channels 32a and 32b lead from the surrounding chamber 30 to a pair of drainage ports 34a, 34b respectively into the drainage channel 36.

The adjustable medical valve 10 further includes a freely rotating magnetic or magnetizable rotor 40 which, as will be discussed in greater detail below, is configured to rotate with an external applied magnetic field. The assembly further includes a pinion gear 40a (FIGS. 2 and 4) on the rotor which drives a series of speed-reducing, torque enhancing gears 42, 44, 46 and 48 to drive an armature plate 50 (FIG. 2). The armature plate 50 includes an inclined surface 52 configured to slide over a complementary inclined surface 28 (FIG. 2) that is bonded to or formed integrally with the diaphragm 26, which causes the diaphragm to deflect depending on where the armature plate 50 is located.

Figure 5A:
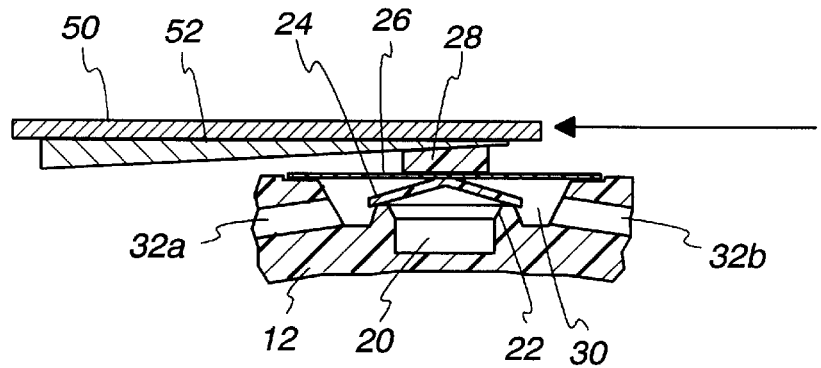
FIG. 5A is a cross-sectional view of the valve and ramps at a first predetermined lower pressure setting.
Figure 5B:
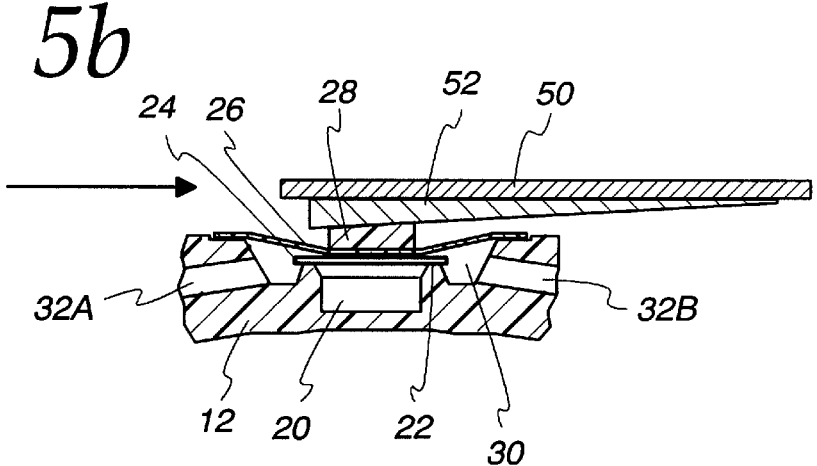
FIG. 5B is a cross-sectional view of the valve and ramps at a second predetermined higher pressure setting.

As seen in FIGS. 5A and 5B, the inclined surface 52 of the armature plate 50 slides over the complementary inclined surface 28 of the diaphragm 26 causing the diaphragm to deflect as the armature plate is rotated. As discussed above, the deflection of the diaphragm governs the pressure regulation set point of the cone-shaped valve 24. FIG. 5A shows the relationship between the complementary inclined surface 28 and the inclined surface 52 that results in the least deflection of the diaphragm and the lowest pressure setting for the cone-shaped valve 24. FIG. 5B illustrates the relationship between the complementary surfaces that results in the greatest deflection of the diaphragm at the highest pressure setting for the cone-shaped valve 24. The pressure regulation set point can be increased or decreased depending on the direction of rotation of an external magnet, as will be discussed in greater detail below, and the adjustment can be repeated any number of times.

Figure 6:
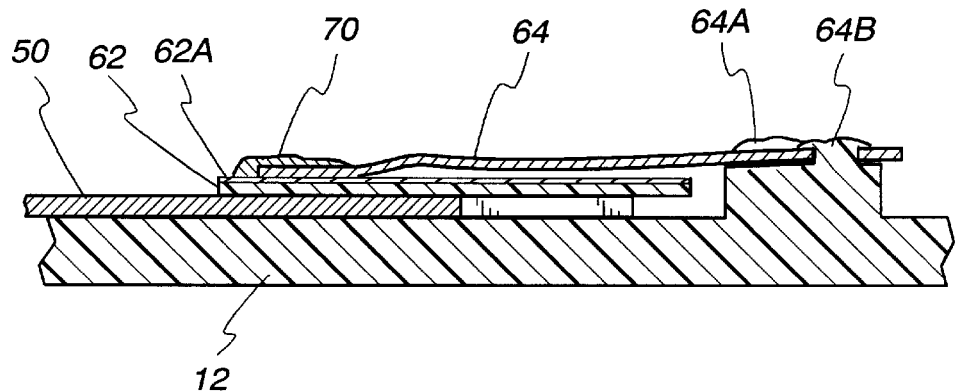
FIG. 6 is a cross-sectional view of the armature plate capacitor dielectric and spring clip.

The adjustable medical valve 10 may further include a resonant circuit configured to monitor the absolute setting of the valve 24; the resonant frequency of the circuit varies according to the setting of the valve 24. According to one embodiment, the resonant circuit includes a fixed inductor and a variable capacitor. The fixed inductor includes one or more loops of wire 60 embedded in a channel molded in the base plate 12 (FIG. 2). The variable capacitor includes a dielectric 62 having one metallized surface 62a that is soldered or bonded to one end 64e of the spring clip 64. The other end of the spring clip near the hose 64a and 64b is attached to the base plate 12. The spring clip 64 presses the dielectric 62 snugly against the armature plate 50 while allowing the armature plate 50 to rotate while the dielectric 62 is held in a fixed position. The metallized surface 62a serves as one of the plates of the capacitor and the armature 50 serves as the other plate, creating a variable capacitor whose capacitance is a function of the angular rotation of the armature 50. As illustrated in FIG. 6, the smallest capacitance is obtained at position A and the greatest capacitance is obtained at position B. The lead wires of the inductive loop 60 are soldered or otherwise bonded to a small tab 74c in the armature 50 and to a small tab 72 on the spring clip 64.

In operation, aqueous humor in the anterior chamber 84 (FIG. 8) of the eye enters the free end 16a of the inlet tube 16 where it passes into the small chamber 20. When the intraocular pressure within the chamber 20 is sufficiently high, the valve 24 opens and permits aqueous humor to escape into the surrounding chamber 30 that is sealed from the interior of the implant by the flexible diaphragm 26. The fluid in the chamber 30 exits via the channels 32a and 32b and drainage ports 34a and 34b, where it is dispersed along the drainage channel 36. The aqueous humor is then absorbed by the sub-Tenon's tissue 85 above the drainage channel 36 and cover 14 of the implant 10.

Figure 10:
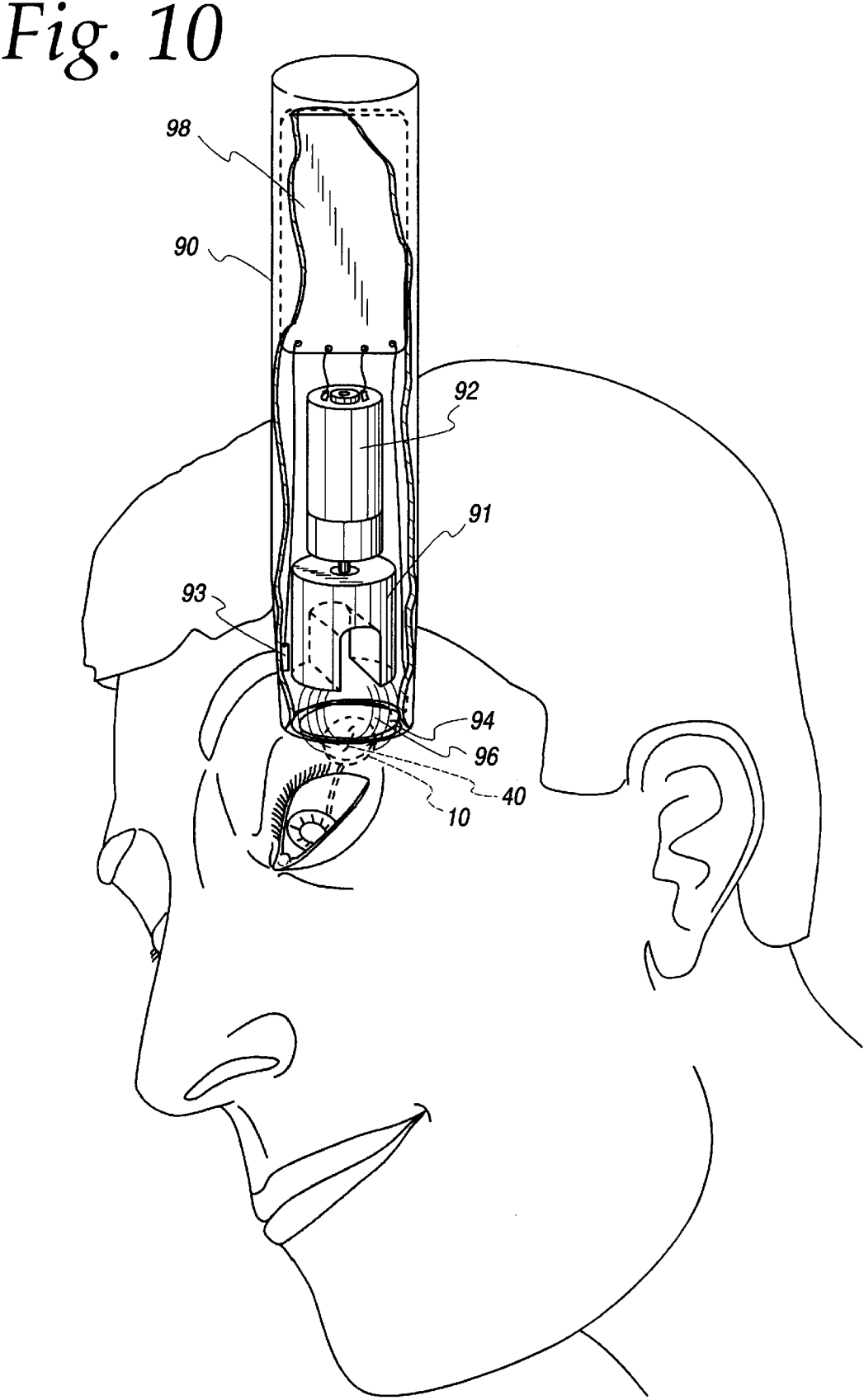
FIG. 10 shows the location and application of a rotating magnet to adjust the implant and a loop antenna to sense the resonant dip frequency that indicates the implant's valve setting.

The pressure differential at which the cone-shaped valve 24 opens and closes is determined by the cross-sectional area defined by the internal rim 22; the thickness and angle of the cone-shaped valve 24; the elasticity of the materials from which the valve is made; and the deflection of the diaphragm 26 to which the apex of the cone-shaped valve is attached. In one embodiment, the pressure regulation set point setting can be adjusted over a span of 5 to 40 mm Hg for a 0.25 mm deflection of the diaphragm 26. The deflection of the diaphragm and thus the pressure regulating set point for the cone-shaped valve 24 can be adjusted non-invasively using an external rotating magnetic field. In particular, as shown in FIG. 10, an external magnet 91 is used for rotating the rotor 40 (FIG. 1) to adjust the valve setting as discussed above. An exemplary external magnet 91 is shown in FIG. 10, shown as a small hand-held instrument 90 with a housing. The rotating magnet 91 may be driven by a small motor and gear drive 92. A Hall effect sensor 93 may be located near the magnet 91 to sense the rotations of the magnet 91 to allow the direction rate and number of rotations to be precisely controlled by a microprocessor or microcontroller (not shown). As discussed above, the rotating magnetic field causes the freely rotating magnetic rotor 40 in the implant to rotate synchronously with the applied external field. The pinion gear 40a on the rotor 40 then drives the series of speed-reducing torque enhancing gears 42, 44, 46 and 48 to drive the armature plate 50, causing it to rotate (in one embodiment) by roughly 30° for approximately 240 rotations of the external magnetic field.

As discussed above, the present invention provides an ability to interrogate the absolute valve setting, thereby verifying that the rotating magnetic field had coupled to the rotor 40 in the implant and that the valve 24 had been successfully adjusted and was not operating near its upper and lower limits. The ability to interrogate the absolute valve setting also provides a self-contained and non-volatile record of the valve setting that does not depend solely on a history of incremental changes for safe and effective use. As discussed above, a resonant circuit in the implant has a resonant frequency which varies according to the setting of the valve. The resonant circuit includes a fixed inductor having one or more loops of wire 60 and a variable capacitor formed from the armature plate 50 and a dielectric 62. The inductive loop of the implant also serves as an antenna and allows the resonant frequency to be externally interrogated by a dedicated resonance absorption sensing circuit or an instrument known as a dip meter (such as the Model MFJ-201 1.5–250 MHz dip meter manufactured by MFJ Enterprises Inc., Starkville, Mo.).

Figure 9A:
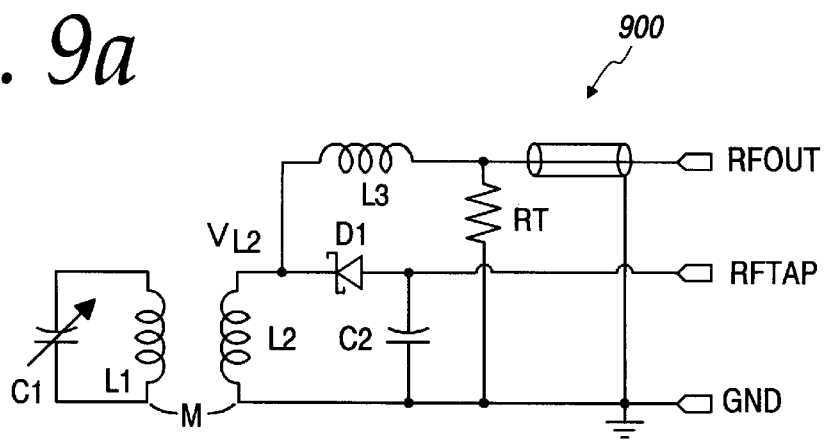
FIG. 9A shows an exemplary resonance absorption dip sensing circuit using an inductive voltage divider and peak detector circuit.
Figure 9B:
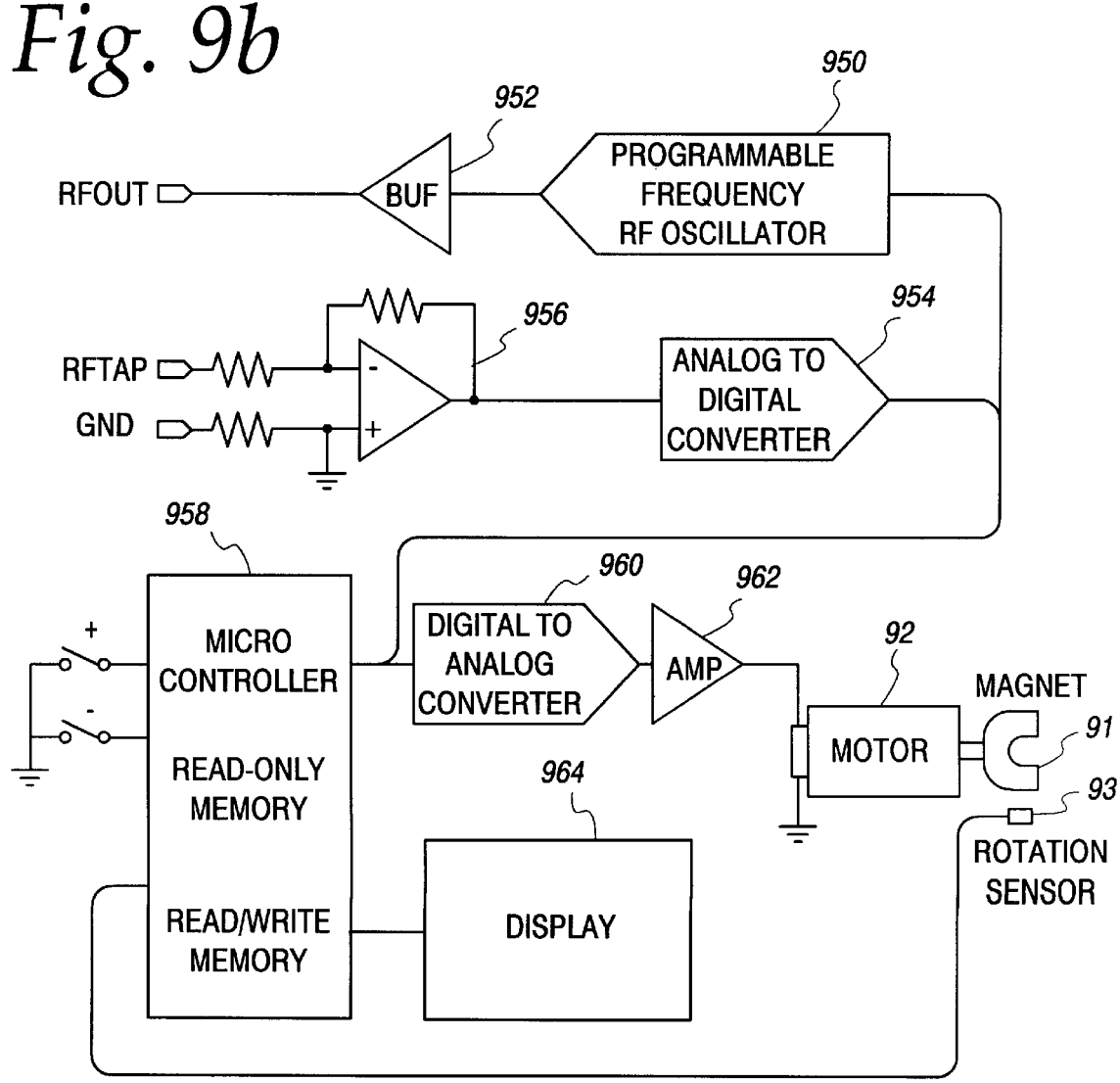
FIG. 9B illustrates a block diagram for the hand-held valve programming instrument.

In an alternate embodiment, however, the rotating magnet and resonance absorption sensing circuit are combined in a single hand-held instrument that both adjusts the implant by providing a rotating magnetic field, interrogates the implant to verify that it has been adjusted thereby providing an easy to use interface for the clinician. As shown in FIGS. 9A and 9B, the resonance sensing circuit 900 uses a voltage divider and a swept radio frequency source 950 to measure the impedance change of the resonant circuit in the implant as a function of frequency. The sensing circuit includes the capacitor C1 and inductor L1 of the implant. One leg of the voltage divider, inductor L2, is a multi-turn spiral loop antenna 94 implemented on a small circuit board 98 located at the tip of the hand-held instrument 90 shown in FIG. 10. The axis of the spiral loop antenna 94 is positioned collinearly with the axis of the inductive loop 60 inside the implant for optimum coupling. The outer leg of the voltage divider inductor L3 is a small air core inductor mounted with its axis perpendicular to L2 to minimize its magnetic coupling to L2 and the inductive loop in the implant. Typical values are 0.1 µH for L2 and 0.2–0.6 µH for L3.

As shown in FIG. 9A, the voltage divider including inductors L2 and L3 is driven by a swept frequency constant amplitude signal RFOUT. If an external tuned circuit such as the implant is not present, the voltage $V_{L2}$ across the inductor L2 is $V_{RFOUT}$ X L2/(L2+L3) and is independent of the excitation frequency. When the inductor L1 of the resonant circuit of the implant is position near L2, the two inductors are coupled by a mutual inductant M and the voltage $V_{L2}$ across inductor L2 exhibits a resonance at frequency $f_0$=(½π) SQRT ((L1+(M²/(L2+L3)))C1). The mutual inductance M can be calculated by noting that $V_{L2}/V_{RFOUT}$=L2/(L3+L2) for f<<$f_0$ and that $V_{L2}/V_{RFOUT}$= (L2−(M²/L1))/(L3+(L2−(M²/L1))) for f>>$f_0$. The inductor L2 can be located within the probe tip to limit the mutual inductance so that M²/(L2+L3)<L1. This ensures that the observed resonant frequency will be close to the unloaded resonant frequency (½π) SQRT (L1 C1) for the implant and that the resonant frequency correction due to the mutual inductance is relatively minor.

As shown in FIG. 9B, the instrument 90 receives the RFTAP input into an amplifier 956, the output of which is provided to an analog to digital converter 954. The A/D converter output is provided to the microcontroller 958. A display 964 is provided, to show number of rotations and other clinically useful information. The microcontroller 958 is coupled to control a programmable RF oscillator 950, the output of which may be buffered 952 and provided to the circuit 900 as RFOUT. In addition, the microcontroller 950 provides signals, via a digital-to- analog converter 960 and amplifier 962, to control the motor 92 and hence the rotation of the magnet 91. A rotation sensor 93 is provided, coupled to the microcontroller 958, for monitoring rotation of the magnet 91.

The amplitude of the voltage $V_{L2}$ across the inductor L2 is measured by a peak detector including the Schottky diode D1 and capacitor C2. The rectified signal RFTAP is sent to the controller board 98 shown in FIG. 9B where it is amplified (956) and converted to digital samples (954). The controller board 98 also provides a resistor to discharge the peak detector capacitor C2. During a typical measurement sequence, the microcontroller 958 slowly increases the frequency of the excitation signal RFOUT and simultaneously measures the rectified signal RFTAP. The microcontroller 958 notes the frequency at which the resonance occurs and verifies that the absolute setting of the valve 24 was changed appropriately during the adjustment process. In addition to the basic functions noted above, the microcontroller 958 performs other functions as well, including verifying that the change in amplitude of the signal RF during resonance is large enough to indicate a valid reading. In addition, the microcontroller 958 compensates for the slight shift in resonant frequency due to the mutual inductance M. Further, it verifies that the resonant frequency of the valve implant change appropriately relative to the direction and number of magnet rotation and ensures that the coupling of the rotating magnetic field to the implant was adequate. Finally, the microprocessor 958 presents the data in clinically useful units for recording and interpretation by the clinician and later comparison with follow-up tonometer measurements.

In general, the materials that make contact with human tissue and fluids are materials that acceptable for implantation in humans. Exemplary materials are as follows: The inlet tube 16 may be made from a pliant biocompatible material, such as silicone, a siliconized rubber material, for example, as manufactured by Dow Corning Corporation, Medical Products Division, under the trade name Silastic. The implant base 12 and cover 14 may be made from a relatively more rigid biocompatible material, such as polymethyl methacrylate (PMMA). An inert metal, such as gold, titanium or other non-magnetic stainless steel or other non-magnetic biocompatible materials may also be used. The diaphragm 20 and conical valve 24 may be made from a pliant biocompatible material such as silicone.

The remaining elements inside the implant do not contact human tissue or fluids, thus biocompatibility is not required. Exemplary materials for these elements are as follows: The armature plate 50 may be made of brass or any other non-ferrous metal. The plate could also be made of plastic; however, the area adjacent to the dielectric 62 would have to be metallized. The dielectric 62 can be made from ceramic or other dielectric material with a relatively high dielectric constant. The spring clip 64 can be made from a resilient non-magnetic metal. The pinion 40A and gears and pinions 42 and 42A, 44 and 44A, 46 and 46A, and 48 and 48A may be made from injection molded plastic, made from injection molded plastic or a non-magnetic metal such as brass. The rotor 40 may be made from a magnetic material with high permeability, such as mu-metal.

The invention described in the above detailed description is not intended to be limited to the specific form set forth herein, but on the contrary, it is intended to cover such alternatives, modifications, and equivalents as can reasonably be included within the spirit and scope of the appended claims.

What is claimed is:

1. A medical implant, comprising:
    a non-invasively adjustable implantable medical valve having open and closed positions, said medical valve being continuously adjustable between said open and closed positions by an external magnetic field; and
    an implanted circuit configured to provide an indication in response to said external magnetic field representative of the position of said valve after it has been implanted.

2. A medical implant according to claim 1, wherein said medical valve includes a rotatable armature responsive to said magnetic field to adjust the position of the medical valve.

3. A medical implant according to claim 2, wherein said medical valve includes a rotor operably coupled to said rotatable armature, and configured to drive said armature responsive to said magnetic field.

4. A medical implant according to claim 1, wherein said circuit includes a resonant circuit.

5. A medical implant according to claim 4, a frequency of said resonant circuit configured to be read by an external device.

6. A system for controlling fluid flow in a body, comprising:
    an implant having an adjustable valve, said valve including means for providing a position indication in response to an external magnetic field of the position of the valve; and
    an external device for non-invasively adjusting the position of said valve in response to said position indication.

7. A system according to claim 6, said valve being magnetically adjustable.

8. A system according to claim 7, said implant including a resonant circuit, said resonant circuit responsive to a setting of said valve.

9. A system according to claim 8, said resonant circuit readable by said external instrument.

10. A system according to claim 7, said valve being adjustable by a rotating magnetic field.

11. A system according to claim 10, said implant including a rotor configured to respond to said rotating magnetic field.

12. A system according to claim 11, said rotor operably coupled to a rotatable armature.

13. A method for controlling an implantable device having an adjustable valve the method comprising:

receiving an electronic signal indicative of the position of the valve in said implantable device;

applying a magnetic field to adjust the position of said valve in said implantable device between an open position and closed position in response to said signal.

14. A method according to claim 13, wherein said magnetic field is applied from external to said device.

15. A method for varying the intraocular pressure of a subject comprising the steps of:

(a) implanting a continuously adjustable valve, said valve configured to relieve said ocular pressure as a function of the position of said valve;

(b) initially setting the position of said valve at the time of the implant;

(c) non-invasively checking the position of the valve after implant; and (d) externally changing the position of the valve in response to the information regarding the position of the valve.

* * * * *